United States Patent [19]

Paltauf et al.

[11] Patent Number: 4,717,512
[45] Date of Patent: Jan. 5, 1988

[54] PREPARATION OF ACYLATED GLYCEROPHOSPHOCHOLINES AND GLYCEROPHOSPHOETHANOLAMINES

[75] Inventors: Friedrich Paltauf; Albin Hermetter, both of Graz, Austria

[73] Assignee: Chemie Linz Aktiengesellschaft, Linz, Austria

[21] Appl. No.: 891,515

[22] Filed: Jul. 29, 1986

Related U.S. Application Data

[62] Division of Ser. No. 733,619, May 13, 1985, Pat. No. 4,622,180.

[30] Foreign Application Priority Data

May 15, 1984 [AT] Austria .................................. 1590/84

[51] Int. Cl.[4] ...................... C07F 9/10; A61K 31/685
[52] U.S. Cl. ................................ 260/389; 260/501.12; 558/169
[58] Field of Search ........................... 260/389, 501.12; 558/169

[56] References Cited

U.S. PATENT DOCUMENTS 4,622,180 11/1986 Paltauf et al. ...................... 260/389

FOREIGN PATENT DOCUMENTS 2020663 11/1979 United Kingdom ................ 558/169
2058792  4/1981 United Kingdom ................ 558/169

OTHER PUBLICATIONS

H. Eibl, Synthesis of Glycerophospholipids, Chemistry and Physics of Lipids (1980), pp. 405–429.
H. Eibl, Phospholipids, Angewandete Chemie (1984), pp. 247–262.
*The Nomenclature of Lipids*, Biochem J. (1978), pp. 21–35.
McOmie, Protective Groups in Organic Chemistry, 1973, pp. 100–103.
Daubert, Jor. of Amer. Chem. Soc., vol. 62, 1940, pp. 1713–1716.

Primary Examiner—Glennon H. Hollrah
Assistant Examiner—Raymond Covington
Attorney, Agent, or Firm—Mark Dryer

[57] ABSTRACT

Preparation of chemically defined pure enantiomeric 1,2-diacyl-sn-glycero-3-phosphocholines and 1,2-diacyl-sn-glycero-3-phosphoethanolamines which are substituted in positions 1 and 2 of the glycerol, by acylation of triphenylmethyl derivatives of sn-glycero-3-phosphocholine and sn-glycero-3-phosphoethanolamine.

1 Claim, No Drawings

PREPARATION OF ACYLATED GLYCEROPHOSPHOCHOLINES AND GLYCEROPHOSPHOETHANOLAMINES

This is a division of application Ser. No. 733,619, filed on May 13, 1985, now U.S. Pat. No. 4,622,180.

The present invention relates to new triphenylmethyl derivatives of sn-glycero-3-phosphocholine and sn-glycero-3-phosphoethanolamine, processes for their preparation, and their use for the synthesis of chemically defined, pure enantiomeric 1,2-diacyl-sn-glycero-3-phosphocholines and 1,2-diacyl-sn-glycero-3-phosphoethanolamines which are substituted in positions 1 and 2 of the glycerol, independently of one another, by different acyl radicals.

In the current state of the art, chemically defined phosphatidylcholines and phosphatidylethanolamines which carry different acyl radicals in positions 1 and 2 of the glycerol are obtainable only via a multistage total synthesis or expensive semisynthetic processes, which require the use of enzymes and a large excess of carboxylic acids. The relevant prior art is described in two review articles by H. Eibl in Chem. Phys. Lipids, Volume 26 (1980), pages 405–429, and in Zeitschrift für Angewandte Chemie [Journal of Applied Chemistry], Volume 96 (1984), pages 247–262.

The industrial-scale synthesis of these phosphatidylcholines and phosphatidylethanolamines, each of which carries different substituents, is not feasible by means of the processes known to date and the starting materials and intermediates used therein.

It was therefore the object of the present invention to start from simple and easily obtainable starting materials and provide new intermediates for a process which permits pure enantiomeric 1,2-diacyl-sn-glycero-3-phosphocholines and 1,2-diacyl-sn-glycero-3-phosphoethanolamines, each of which carries different substituents and has a defined chemical structure, to be prepared in an economical and time-saving manner on an industrial scale. This object was achieved by the present invention in an unexpectedly simple and effective manner.

The present invention accordingly relates to the new triphenylmethyl derivatives of sn-glycero-3-phosphocholine and sn-glycero-3-phosphoethanolamine of the formula

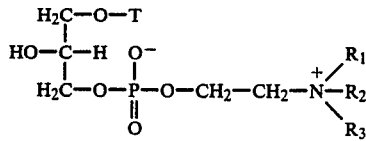

in which
T denotes an unsubstituted or substituted triphenylmethyl group and the radicals
$R_1$, $R_2$ and $R_3$ either are identical and each represent a methyl group or are different, in which case two of the radicals $R_1$, $R_2$ and $R_3$ always denote hydrogen and the third radical represents an unsubstituted or substituted triphenylmethyl group.

The compounds of the formula I in which $R_1$, $R_2$ and $R_3$ each denote methyl are derivatives of glycerophosphocholine, while the compounds of the formula I in which two of the radicals $R_1$, $R_2$ and $R_3$ denote hydrogen and the third represents a substituted or unsubstituted triphenylmethyl group constitute derivatives of glycerophosphoethanolamine.

In the general formula I, the radical denoted by T in the compounds according to the invention, and one of the radicals $R_1$, $R_2$ and $R_3$, where the other two radicals denote hydrogen, are each preferably an unsubstituted triphenylmethyl group. However, the general formula I also embraces those compounds in which the 1-O-triphenyl-methyl group, and/or any N-triphenylmethyl group which may be present in the molecule, independently of one another are monosubstituted or polysubstituted by alkyl radicals, such as methyl, ethyl, propyl and the like, alkoxy radicals, such as methoxy, ethoxy, propoxy and the like, or halogen, such as fluorine, chlorine or bromine. Among the compounds of the formula I containing substituted triphenylmethyl groups, preferred compounds are in turn those in which one or more phenyl radicals of the triphenylmethyl groups are substituted in the para-position by alkoxy radicals having 1 to 6 carbon atoms.

In the compounds of the formula I, the 1-O-triphenylmethyl group and any N-triphenylmethyl group which may be present in the molecule, are protecting groups which are eliminated during the preparation of 1,2-diacyl-sn-glycero-3-phosphocholines and 1,2-diacyl-sn-glycero-3-phosphoethanolamines. Therefore, the meaning and the number of the substituents on the triphenylmethyl groups in the compounds of formula I are of minor interest, as long as the triphenylmethyl protecting groups can be easily removed by the action of acids.

The nomenclature and designation of positions used in the present description for glycerophosphocholine, glycerophosphoethanolamine and their derivatives follow the rules stated in Biochem. J. 171, 29–35 (1978). The abbreviation "sn" in the systematic chemical names of the compounds mentioned denotes "stereospecifically numbered". All designations of positions in the present description which relate to the position of the substituents on the glycerol radical are based on this stereospecific numbering.

The compounds of the general formula I are prepared by a method in which sn-glycero-3-phosphocholine or sn-glycero-phospho-(N-triphenylmethyl)-ethanolamine of the general formula

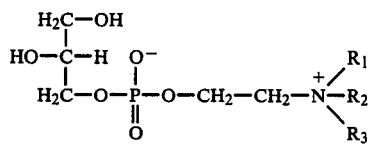

in which
$R_1$, $R_2$ and $R_3$ have the meanings given above, their salts with inorganic or organic acids or bases, or their complexes with metal salts are tritylated at the oxygen in position 1 of the glycerol by reaction with a reactive triphenylmethyl derivative of the general formula $$T-X \qquad III$$

in which
T is defined as in formula I and
X denotes a reactive leaving group, such as chlorine, bromine or iodine,
in an inert organic solvent or solvent mixture at temperatures from room temperature to the boiling point of the solvent or of the lowest-boiling solvent component of the solvent mixture.

The tritylating agent used in the process according to the invention is a reactive triphenylmethyl derivative, preferably triphenylmethyl chloride or triphenylmethyl bromide, particularly preferably triphenylmethyl chloride. For the preparation of the 1-O-triphenylmethyl derivative of the general formula I, one mole equivalent of the tritylating agent is consumed. Although advantageous in many cases for accelerating the course of the reaction and for completing the reaction, it is not absolutely necessary to employ an excess of the tritylating agent. The amount of tritylating agent employed can be varied within wide limits, as desired. The use of a small excess to a several-fold molar excess of tritylating agent per mole of the starting material of the formula II has proved particularly useful, a 1.5-fold to 3-fold molar excess being particularly preferred.

The reaction of the compound of the formula II with that of the formula III is advantageously carried out in the presence of an excess of a suitable proton acceptor. Suitable proton acceptors are inorganic or organic bases. The reaction is particularly preferably carried out in the presence of organic bases, such a tertiary amines, for example trimethylamine, triethylamine, N-methylpiperidine, N,N-dimethylaniline or N,N-diethylaniline, Hünig's base or heterocyclic bases, for example pyridine, 4-N,N-dimethylaminopyridine, 4-pyrrolidinopyridine, picolines, collidine, quinoline, isoquinoline and the like.

The reaction is carried out in organic solvents or solvent mixtures which are inert to the particular reactants. Particularly suitable solvents are aprotic, polar solvents. These preferably include dimethyl sulfoxide, carboxamides, such as dimethylformamide, dimethylacetamide, hexamethylphosphorotriamide or N-methylpyrrolidone, nitriles, such as acetonitrile or propionitrile, heterocyclic bases, such as pyridine, quinoline or picolines, or mixtures of such solvents. In many cases, it may be advantageous to carry out the reaction in a solvent mixture consisting of an inert aprotic polar solvent and an inert aprotic solvent of low polarity. Examples of solvent components of low polarity which are suitable for such solvent mixtures are aliphatic or aromatic hydrocarbons, such as low-boiling or high-boiling petroleum ether, hexane, heptane, benzene, toluene and the like, halogenated aliphatic or aromatic hydrocarbons, such as methylene chloride, chloroform, 1,2-dichloroethane, carbon tetrachloride, chlorobenzene, p-chlorotoluene and the like.

The reaction temperatures can be varied within a wide range. In general, the reaction is carried out at temperatures between room temperature and the boiling point of the particular solvent employed or of the lowest-boiling solvent component of the solvent mixture used, preferably at temperatures between 20° C. and 200° C., in particular at temperatures between 20° and 80° C.

To prepare the compounds of the general formula I, it is possible to start from the compounds of the general formula II as such, from their salts with inorganic or organic acids or bases, or from their complexes with metal salts. Particularly in the preparation of 1-O-tritylsn-glycero-3-phosphocholine, it may be advantageous in many cases to employ the more stable metal salt complexes having a longer shelf life, for example the cadmium chloride adduct of sn-glycero-3-phosphocholine.

Working up is advantageously carried out by evaporating down the reaction solution or precipitating the products from the reaction solution by dilution with solvents in which the compounds of the general formula I are poorly soluble. The crude products obtained by conventional chemical working-up methods are very suitable, without further purification operations, as intermediate compounds for the preparation of phosphatidylcholines and phosphatidylethanolamines, each of which carries different substituents. Particularly suitable methods for purifying the compounds of the general formula I are the conventional chromatographic methods, such as preparative thin-layer chromatography, column chromatography, adsorption chromatography, medium pressure liquid chromatography or high pressure liquid chromatography.

The invention furthermore relates to the use of the new compounds of the general formula I for the preparation of pure enantiomeric phosphatidylcholines and phosphatidylethanolamines which carry different acyl radicals in positions 1 and 2 of the glycerol, independently of one another.

The compounds of the formula I can preferably be used in a method for preparing 1,2-diacyl-sn-glycero-3-phosphocholines and 1,2-diacyl-sn-glycero-3-phosphoethanolamines of the formula

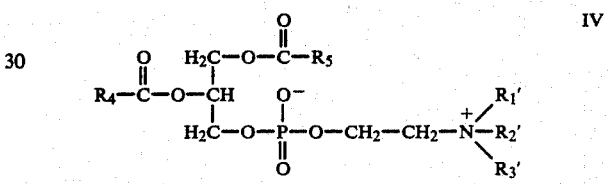

in which $R_1'$, $R_2'$ and $R_3'$ are identical and in each case denote either 3 hydrogen atoms or 3 methyl groups, and $R_4$ and $R_5$ are different and independently of one another denote a straight chain or branched $C_1$ to $C_{24}$-alkyl radical, a straight chain or branched $C_1$ to $C_{24}$-alkyl radical substituted by one or more halogen atoms or alkoxy groups, a straight chain or branched monounsaturated or polyunsaturated $C_3$ to $C_{24}$-alkenyl radical or a stright chain or branched monounsaturated or polyunsaturated $C_3$ to $C_{24}$-alkenyl radical substituted by one or more halogen atoms or alkoxy groups, which method comprises (a) acylating a compound of the formula I by reaction with an acylating derivative of a carboxylic acid of the formula $R_4COOH$ to give a compound of the formula

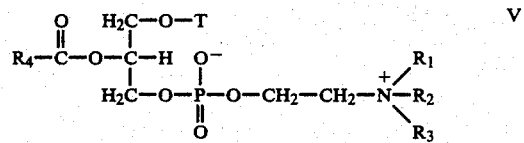

wherein

T represents an unsubstituted or substituted triphenylmethyl group and $R_1$, $R_2$ and $R_3$ either are identical and each represent a methyl group or are different, in which case two of the radicals $R_1$, $R_2$ and $R_3$ always denote hydrogen and the third radical represents an unsubstituted or substituted triphenylmethyl group, (b) eliminating the 1-O-triphenylmethyl group from the resulting compound of the formula V by the action of acids, with the proviso that, in the case of compounds of formula V in which one of the radicals $R_1$, $R_2$ and $R_3$ is a triphenylmethyl group, the acid is a Lewis acid, with formulation of a 2-acyl-sn-glycero-3-phosphocholine or a 2-acyl-sn-glycero-3-phospho-(N-triphenylmethyl)-ethanolamine of the formula

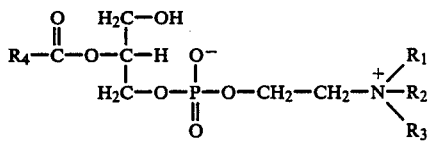

VI in which $R_1$, $R_2$, $R_3$ and $R_4$ have the meaning given above, (c) acylating the compound of the formula VI by reaction with an acylating derivative of a carboxylic acid of the formula $R_5$—COOH to give a 1,2-diacyl-sn-glycero-3-phosphocholine or 1,2-diacyl-sn-glycero-3-phospho-(N-triphenylmethyl)-ethanolamine of the formula

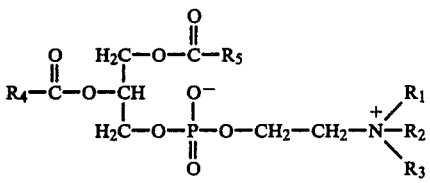

VII in which $R_1$, $R_2$ and $R_3$ are defined as in formula V, and $R_4$ and $R_5$ have the meaning given in formula IV, and (d) eliminating any N-triphenylmethyl group present in the compound of the formula VII by the action of an acid in an aprotic solvent.

In the definitions given in the present description for $R_4$ and $R_5$, a "straight-chain or branched alkyl radical" is understood as meaning a saturated aliphatic hydrocarbon radical which contains 1 to 24 carbon atoms and can be branched as often as desired. The expression "straight-chain or branched, monounsaturated or polyunsaturated alkenyl radical" represents an unsaturated aliphatic hydrocarbon radical which has 3 to 24 carbon atoms and one or more olefinic double bonds and can likewise be branched as often as desired. Both in the alkyl radicals and in the alkenyl radicals, one or more hydrogen atoms can be replaced with halogen, such as fluorine, chlorine, bromine or iodine, or with alkoxy radicals, such as methoxy, ethoxy, propoxy, isopropoxy, butoxy and the like.

The acylation of compounds of the general formula I to give the 2-acyl derivatives of the general formula V is carried out using reactive derivatives of carboxylic acids of the general formula $R_4COOH$. Examples of suitable acylating agents of this type are halides, anhydrides, active esters and azolides of these carboxylic acids, carboxylic acid imidazolides being particularly preferred. The reaction is carried out under the conventional acylation conditions, for example in anhydrous, polar aprotic solvents or solvent mixtures which are inert to the particular reactants. These preferably include ethers, such as tetrahydrofuran, dioxane or ethylene glycol dimethyl ether, halogenated aliphatic or aromatic hydrocarbons, such as methylene chloride, chloroform, 1,2-dichloroethane, chlorobenzene or p-chlorotoluene, carboxamides, such as dimethylformamide or dimethylacetamide, hexamethylphosphorotriamide, N-methylpyrrolidone, dimethyl sulfoxide, heterocyclic bases which at the same time act as proton acceptors, such as pyridine, alkylated pyridines, N,N-dialkylaminopyridines and the like, or mixtures of these solvents. When carboxylic acid imidazolides are used as acylating agents, mixtures of dimethyl sulfoxide and tetrahydrofuran in a ratio of 1:4 to 4:1 have proved particularly useful. The acylation is advantageously carried out using an acid acceptor which simultaneously acts as a catalyst and is of inorganic nature, such as sodium hydride, metallic sodium and the like, or of organic nature, such as triethylamine, N-methylpiperidine, N,N-dimethylaniline or N,N-diethylaniline, or in the presence of heterocyclic bases, such as pyridine, N,N-dimethylaminopyridine, picolines, collidine, quinoline, isoquinoline and the like. The acylation reaction can be carried out at temperatures between 0° C. and the boiling point of the solvent, but is preferably effected at temperatures between 20° C. and 30° C.

The unconverted carboxylic acids obtained in the reaction, and any unreacted residues of acylating agents still present, must be separated off before the subsequent reaction step, for example by chromatography over silica gel or by other purification methods conventionally used in preparative chemistry, such as by extraction of a solution of the crude product in water-immiscible solvents with dilute aqueous bases, for example aqueous ammonia, or by recrystallization or reprecipitation of the crude product from suitable solvents.

The 1-O-triphenylmethyl group is then eliminated from the 2-acyl derivatives of the general formula V by treatment with an acid. In eliminating the 1-O-triphenylmethyl group, the use of a Lewis acid is necessary in the case of the glycerophosphoethanolamine derivatives of the general formula VI in which one of the radicals $R_1$, $R_2$ and $R_3$ denotes a triphenylmethyl radical in order to retain the N-triphenylmethyl group, and is advantageous in the case of the glycerophosphocholine derivatives of the formula V in which the radicals $R_1$, $R_2$ and $R_3$ each denote methyl. Elimination of the 1-O-triphenylmethyl group in the case of the glycerophosphocholine derivatives can, however, also be effected with inorganic acids, for example mineral acids, such as hydrochloric acid, hydrobromic acid, perchloric acid and the like, or with organic acids, such as trifluoroacetic acid or trichloroacetic acid and the like. To prevent migration of an acyl grup, it is advantageous to maintain temperatures below 20° C. The boron trifluoride/methanol complex in methylene chloride is employed at 0° C., this being a particularly effective detritylation agent. The compounds of the general formula VI are obtained in this procedure in such good purity that they do not need to be subjected to any further purification operations before further processing. The embodiment of the synthesis in which the compounds of the general formula VI which are obtained after elimination of the 1-O-triphenylmethyl group are fed directly for further acylation is particularly advantageous since any acyl migrations which may occur during the purification operations are decisively reduced at this stage of the synthesis.

Further acylation of compounds of the general formula VI to give the 1,2-diacyl derivatives of the general formula IVa is again carried out using one of the abovementioned reactive carboxylic acid derivatives of the acids of the general formula R₅COOH. To introduce the acyl radical into position 1 of the glycerol, carboxylic anhydrides have proved particularly useful in this case. The reaction is carried out under the conventional acylation conditions, advantageously in anhydrous, polar aprotic solvents or solvent mixtures, suitable solvents being not only the solvents stated above for the acylation of the 2-position but also solvent mixtures containing halogenated hydrocarbons, such as methylene chloride, chloroform, carbon tetrachloride, chlorobenzene and the like. Mixtures which have proved particularly useful are mixtures of methylene chloride and 4-N,N-dimethylaminopyridine, which at the same time acts as an acid acceptor. The temperature range from room temperature to the boiling point of the solvent or of the lowest-boiling solvent component can be chosen for the reaction. Preferably, the reaction is carried out at room temperature or slightly elevated temperatures of 20° to 40° C.

The diacyl derivatives of the general formula VII which are formed can be obtained in pure form by means of the purification operations usually employed in preparative chemistry. Thus, for example, the crude products can be dissolved in water-immiscible solvents and freed from excess acylating agents by extraction with dilute aqueous bases, for example with aqueous ammonia, or can be purified by recrystallization or reprecipitation.

The conventional chromatographic methods or multiplicative partition between two phases are also suitable for the purification of the compounds of the formula VII.

The 1,2-diacyl-sn-glycero-3-phosphoethanolamines of the formula IV, wherein $R_1'$, $R_2'$ and $R_3'$ each denote hydrogen, can be obtained from compounds of the formula VII in which one of the radicals $R_1$, $R_2$ or $R_3$ denotes a triphenylmethyl group, by elimination of the N-triphenylmethyl radical. The elimination reaction can be carried out using inorganic acids, for example mineral acids, such as hydrochloric acid or hydrobromic acid, or preferably organic acids, for example halogenated carboxylic acids, such as trichloro- or trifluoroacetic acid, the reaction being carried out in aprotic solvents in order to avoid deacylation in positions 1 and 2 of the glycerol. Preferably, the N-triphenylmethyl radical is removed using trifluoroacetic acid in methylene chloride at temperatures of about 0° C.

The compounds described here are characterized, and their purity is checked, by means of thin-layer chromatography and spectroscopic methods, in particular ¹H-NMR spectroscopy. The spectroscopic data determined are in agreement with the chemical structures described for the compounds.

The compounds of the general formula I are new, central intermediates for the universal chemical synthesis of 1,2-diacyl-sn-glycero-3-phosphocholines and 1,2-diacyl-sn-glycero-3-phosphoethanolamines of the general formula IV, each of which carries different substituents. When intermediates of the general formula 1 are employed, it is no longer necessary to use enzymes, which previously had to be employed in the semi-synthetic preparation of such phosphatidylcholines and phosphatidylethanolamines, each of which carries different substituents; hence, the compounds of the general formula IV are also easily obtainable on an industrial scale. Other advantages of this invention are that the carboxylic acid derivatives used for the acylation in position 1 or in position 2 are virtually completely utilized. In the enzymatic methods used to date, the positions 1 and 2 in the glycerophosphocholine or in N-protected glycerophosphoethanolamines are first substituted by two identical acyl radicals, after which the acyl radical in position 2 is eliminated by the action of phospholipase $A_2$, and the desired acyl radical is introduced into this intermediate by means of a further acylation reaction. In this procedure, the carboxylic acid used for the first acylation in position 2 is lost. Furthermore, the rate and efficiency of the enzymatic hydrolysis depend on the type of carboxylic acid, whereas the preparation, according to the invention, of the compounds of the formula IV is completely independent of this.

The phosphatidylcholines and phosphatidylethanolamines of the general formula IV are, for example, valuable emulsifiers in the preparation of medicaments and crop protection agents or can be used in the photographic industry. These compounds can also be used as chemically defined starting materials for the preparation of liposomes liposome solutions and liposome gels.

sn-Glycero-3-phosphocholine or sn-glycero-3-phospho-(N-triphenylmethyl)-ethanolamine is used as a starting material for the preparation of the compounds of the general formula I. sn-Glycero-3-phosphocholine can be prepared in a simple manner in virtually unlimited amounts of conventional methods, for example by alkaline hydrolysis of natural lecithin. Preferably, commercially available products are used.

sn-Glycero-3-phospho-(N-triphenylmethyl)-ethanolamine is readily obtainable by N-tritylation of sn-glycero-3-phosphoethanolamine from any source. sn-Glycero-3-phospho-(N-triphenylmethyl)-ethanolamine is prepared in a particularly advantageous and simple manner by tritylation of phosphatidylethanolamine in a mixture of phospholipids of vegetable, animal or microbial origin with a reactive triphenylmethyl derivative, preferably triphenylmethyl bromide, followed by hydrolysis of the total lipids. The sn-glycero-3-phospho-(N-triphenyl-methyl)-ethanolamine can be separated from water-soluble cleavage products by extracting it from this mixture with water-immiscible solvents, preferably with chloroform in the presence of methanol, and can then be obtained in pure form by washing out the fatty acids with an alkaline aqueous phase, if appropriate mixed with methanol. sn-Glycero-3-phospho-(N-triphenylmethyl)-ethanolamine can be prepared, for example, by the following procedure:

1.5 g of soya phospholipids and 1.4 g of triphenylmethyl bromide are dissolved in 50 ml of chloroform. After the addition of 1.1 g of triethylamine, the reaction mixture is stirred for 12 hours at 20° C. 50 ml of chloroform and 100 ml of a 0.5N sodium hydroxide solution in methanol are then added, and stirring is continued for 30 minutes at 20° C. 100 ml of chloroform are then added, and the organic phase is separated off and washed three times with an alkaline aqueous phase. Finally, the organic solvent is stripped off in vacuo. The residue, which contains the sn-glycero-3-phospho-(N-triphenylmethyl)-ethanolamine can be used directly for the subsequent O-tritylation. The pure compound, which is obtained by chromatographing the crude product over silica gel with a chloroform/methanol gradient, shows a single spot with $R_f$ 0.3 in thin-layer chromatography over silica gel (mobile phase: 50:25:6 (v/v/v) chloroform-methanol-25% $NH_3$ mixture).

The examples below serve to illustrate the invention in more detail without restricting it.

(a) PREPARATION OF COMPOUNDS OF THE GENERAL FORMULA I

EXAMPLE 1

1-O-Triphenylmethyl-sn-glycero-3-phosphocholine 5 g of sn-glycero-3-phosphocholine/$CdCl_2$ complex and 4.6 g of triphenylmethyl chloride are dissolved in anhydrous dimethylformamide (50 ml) at 70° C. After the addition of 2.3 ml of triethylamine, the mixture is stirred for 30 minutes at 70° C. in the absence of moisture. When the reaction mixture has cooled, 5 g of powdered $NaHCO_3$ are added, and the mixture is stirred for 20 minutes at room temperature. The reaction solution is then filtered, and 300 ml of diethyl ether are added. The oil formed is separated off by centrifuging, washed once with diethyl ether and finally dissolved in 150 ml of methanol. After the addition of 300 ml of $CHCl_3$, washing is carried out using 90 ml of a solvent mixture (upper phase) consisting of 3:48:47 (v/v/v) $CHCl_3/CH_3OH/H_2O$, and the lower phase is diluted with 150 ml of 2:1 (v/v) $CHCl_3/CH_3OH$. 3 ml of 25% strength aqueous $NH_3$ solution are then added, and the mixture is left to stand for 15 minutes at room temperature and finally separated off from the resulting colorless precipitate by centrifuging. When the solvent has been stripped off in vacuo, the oily residue is digested with three times 50 ml of diethyl ether. This procedure gives a yellowish solid crude product (5.5 g) which, when subjected to thin-layer chromatography over silica gel (mobile phase: 65:35:5 (v/v/v) $CHCl_3/CH_3OH/25\%$ $NH_3$ mixture), shows an $R_f$ value of 0.15 and is found to contain only very small amounts of impurities. The pure compound is obtained by medium pressure chromatography over silica gel. A $CHCl_3/CH_3OH$ gradient is used for the elution, the eluant containing 0.5% by volume of 25% strength aqueous $NH_3$ solution. When subjected to thin-layer chromatography over silica gel (mobile phase as for the analysis of the crude product), the pure substance exhibits a single spot at $R_f$ 0.15.

$^1$H-NMR spectrum: δ ppm
3.1 (N—$CH_3$); 3.3–4.3 (choline and glycerol); 7.25 (triphenylmethyl C—H).

EXAMPLE 2

1-O-Triphenylmethyl-sn-glycero-3-phospho-(N-triphenylmethyl)-ethanolamine 946 mg of sn-glycero-3-phospho-(N-triphenylmethyl)-ethanolamine and 1.735 g of triphenylmethyl chloride in 32 ml of anhydrous pyridine are stirred for 48 hours at room temperature in the absence of moisture. The mixture is then poured onto ice water. The product is extracted with three portions of diethyl ether. The combined ether phases are washed twice with water and then dried over $Na_2SO_4$. When the solvent has been stripped off in vacuo, the remaining pyridine is removed by evaporating the residue in the presence of toluene and in vacuo. The residue is taken up in 30 ml of a 1:1 (v/v) chloroform/methanol mixture, and the solution is left to stand overnight at 4° C. After the precipitated triphenylcarbinol has been filtered off and the solvent mixture then stripped off, 1.7 g of crude product are obtained, which is used directly for the subsequent acylation. Chromatography over silica gel with a chloroform/methanol gradient gives the pure compound which shows a single spot at $R_f$ 0.6 when subjected to thin-layer chromatography over silica gel (mobile phase: 6:4 (v/v) chloroform/methanol mixture).

$^1$H-NMR spectrum: δ ppm (DMSO-$d_6$)
3.5–4.3 (glycerol and ethanolamine C—H, diffuse); 7.25 (triphenylmethyl C—H, m).

EXAMPLE 3

Using the method stated in Example 1, the following compound was obtained:

1-O-(4,4'-dimethoxytriphenylmethyl)-sn-glycero-3-phosphocholine

The thin-layer chromatogram over silica gel (mobile phase: 65:35:5 (v/v/v) $CHCl_3/CH_3OH/25\%$ strength aqueous $MH_3$ mixture) shows a single spot, $R_f$ value 0.15.

$^1$H-NMR spectrum: δ ppm ($CD_3OD$)
3.1 (N—$CH_3$); 3.8 (phenyl—O—$CH_3$); 3.3–4.3 (choline and glycerol); 7.23 (aromatic).

EXAMPLE 4

1-O-(4,4'-Dimethoxytriphenylmethyl)-sn-glycero-3-phospho-(N-triphenylmethyl)-ethanolamine A solution of 2.4 g of sn-glycero-3-phospho-(N-triphenylmethyl)-ethanolamine and 4.5 g of 4,4'-dimethoxytriphenylmethyl chloride in 80 ml of anhydrous pyridine is stirred for 72 hours at room temperature. After the pyridine has been stripped off in vacuo, the residue is dissolved in 200 ml of 2:1 (v/v) $CHCl_3/CH_3OH$. This solution is washed with twice 40 ml of 3:48:47 (v/v/v) $CHCl_3/CH_3OH/H_2O$, and the solvent is then distilled off in vacuo. This procedure gives a brown oil which, when digested with 80 ml and 30 ml portions of diethyl ether, gives 2.5 g of the crude product as a colorless amorphous powder. Thin-layer chromatography over silica gel (mobile phase: 6:4 (v/v) $CHCl_3/CH_3OH$ mixture) shows that the crude product contains more than 90% of the desired product ($R_f$ 0.6), which can be used, without further purification, for the preparation of the pure enantiomeric, 1,2-diacyl-sn-glycero-3-phosphoethanolamines, each of which carries different substituents.

The pure compound is obtained by medium pressure chromatography over silica gel with a $CHCl_3/CH_3OH$ gradient (in the presence of 0.5% by volume of aqueous $NH_3$) and shows a single spot at $R_f$ 0.6 in the thin-layer chromatogram (conditions as in Example 3).

$^1$H-NMR spectrum: δ ppm
(2:1 (v/v) $CDCl_3/CD_3OD$)
3.1 (N$^+$—$CH_3$); 3.8 (phenyl—O—$CH_3$); 3.3–4.3 (choline and glycerol); 7.23 (aromatic).

(b) USE OF THE COMPOUNDS OF THE GENERAL FORMULA I, OBTAINED ACCORDING TO THE ABOVE EXAMPLES, FOR THE PREPARATION OF COMPOUNDS OF THE GENERAL FORMULA IV

EXAMPLE 5

(A) 1-O-Triphenylmethyl-2-oleoyl-sn-glycero-3-phosphocholine 1.26 g of oleic acid are allowed to react with 794 mg of carbonyldiimidazole in 25 ml of tetrahydrofuran for 45 minutes at room temperature, after which the solvent is removed in vacuo. A solution of 1.1 g of the crude product obtained from 1-O-triphenyl-methyl-sn-glycero-3-phosphocholine (according to Example 1) in 28 ml of dimethyl sulfoxide is than added to the residue, which contains the fatty acid imidazolide formed. After the addition of a catalyst, which is prepared by dissolving 148 mg of metallic sodium in 11.5 ml of dimethyl sulfoxide, the reaction mixture is allowed to stand for 20 minutes at 20° C., with occasional shaking. Finally, 64 ml of a 0.1N aqueous acetic acid are added all at once. The mixture is extracted twice with a 2:1 (v/v) chloroform/methanol mixture, and the combined organic phases are washed twice with a 1:1 (v/v) methanol/H$_2$O mixture. After the solvent has been evaporated off in vacuo, the crude product is dissolved in chloroform, and the solution is introduced onto a silica gel column. The pure compound (1.1 g) is eluted with a chloroform/methanol gradient, and thin-layer chromatography over silica gel (mobile phase: 65:35:5 (v/v/v) chloroform/methanol/25% NH$_3$) gives a single spot ($R_f$ 0.4).

(B) 2-Oleoyl-sn-glycero-3-phosphocholine 0.5 ml of a 20% strength solution of boron trifluoride in methanol is added to a solution of 500 mg of 1-O-triphenylmethyl-2-oleoyl-sn-glycero-3-phosphocholine in 30 ml of methylene chloride, after which the mixture is stirred for 30 minutes at 0° C. 15 ml of methanol and 9 ml of water are then added, the mixture is shaken to effect extraction, and the organic phase is isolated. The solvent is removed by stripping it off in a high vacuum at room temperature.

(C) 1-Palmitoyl-2-oleoyl-sn-glycero-3-phosphocholine

The residue, which contains the resulting 2-oleoyl-sn-glycero-3-phosphocholine, is dissolved in 30 ml of dry chloroform. 820 mg of palmitic anhydride and 200 mg of dimethylaminopyridine are then added to this solution, and the reaction mixture is stirred for 6 hours at 20° C. Thereafter, 15 ml of methanol are added, and the mixture is extracted by shaking, first with 0.1N HCl and then with H$_2$O. After the organic solvent has been stripped off in vacuo, the substance is purified by chromatography over silica gel, using a chloroform/methanol gradient. The purified compound (400 mg) gives a single spot ($R_f$ 0.4) when subjected to thin-layer chromatography over silica gel (mobile phase: 65:35:5 (v/v/v) chloroform/methanol/25% strength NH$_3$).

EXAMPLE 6

1-Stearoyl-2-oleoyl-sn-glycero-3-phosphocholine

A solution of 2-oleoyl-sn-glycero-3-phosphocholine (obtained as described in Example 5, stages A and B) is reacted with 1.2 g of stearic anhydride according to the method stated in Example 5, stage C, and the product is purified chromatographically and analyzed. 550 mg (76% yield, relative to 1-O-triphenylmethyl-sn-glycero-3-phosphocholine) of 1-stearoyl-2-oleoyl-sn-glycero-3-phosphocholine are obtained, this product giving a single spot in the thin-layer chromatogram over silica gel (mobile phase: 65:35:5 (v/v/v) chloroform/methanol/25% strength aqueous NH$_3$ solution); $R_f$ value 0.4.

EXAMPLE 7

(A) 1-O-Triphenylmethyl-2-linoleoyl-sn-glycero-3-phosphocholine 600 mg of 1-O-triphenylmethyl-sn-glycero-3-phosphocholine (according to Example 1) are acylated according to the method stated in Example 5, stage A, with linoleoylimidazolide, which was prepared from 690 mg of linoleic acid and 440 mg of carbonyldiimidazole. After medium pressure chromatography over silica gel, the pure compound (690 mg, yield 75% of theory) shows a single spot ($R_f$ value 0.3) in the thin-layer chromatogram over silica gel (mobile phase: 65:35:5 (v/v/v) chloroform/methanol/25% strength aqueous NH$_3$ solution).

(B) 2-Linoleoyl-sn-glycero-3-phosphocholine

In order to eliminate the 1-O-triphenylmethyl radical, a solution of 1 g of 1-O-triphenylmethyl-2-linoleoyl-sn-glycero-3-phosphocholine in 60 ml of methylene chloride is treated with a 20% strength solution of boron trifluoride in methanol, as stated in Example 5, stage B.

(C) 1-Stearoyl-2-linoleoyl-sn-glycero-3-phosphocholine

The 2-linoleoyl-sn-glycero-3-phosphocholine obtained in stage B is reacted with 1.6 g of stearic anhydride by the method stated in Example 5, stage C, and the product is purified by chromatography. 820 mg (80% yield, relative to 1-O-triphenylmethyl-sn-glycero-3-phosphocholine) of pure product are obtained, which gives a single spot in the thin-layer chromatogram over silica gel (mobile phase: 65:35:5 (v/v/v) chloroform/methanol/25% strength aqueous NH$_3$ solution); $R_f$ value 0.4.

EXAMPLE 8

(A) 1-O-Triphenylmethyl-2-acetyl-sn-glycero-3-phosphocholine 320 mg of 1-O-triphenylmethyl-sn-glycero-3-phosphocholine (according to Example 1) are reacted with 0.7 ml. of acetic anhydride in 4 ml of anhydrous pyridine overnight at room temperature. The reaction mixture is then poured onto ice water and extracted twice with chloroform/methanol (2:1, v/v). The combined organic phases are washed twice with chloroform/methanol/water (3:48:47 v/v/v), dried over sodium bicarbonate and finally brought to dryness. The crude product is purified by medium pressure chromatography over silica gel, using a chloroform/methanol gradient. The pure product (180 mg, 51% yield) gives a single spot in the thin-layer chromatogram over silica gel (mobile phase: 65:35:5 (v/v/v) chloroform/methanol/25% strength aqueous NH$_3$ solution); $R_f$ 0.16.

$^1$H-NMR spectrum $\delta$ ppm (CDCl$_3$—CD$_3$+OD, 2:1 v/v) 2.13 (H$_3$C—CO, s, 3H); 3.16 (H$_3$C—N, s, 9H); 3.3–4.4 (glycerol and choline—CH$_2$); 5.23 (glycerol C—H, 1H); 7.33 (aromatic, 15H)

(B) 2-Acetyl-sn-glycero-3-phosphocholine (C) 1-Palmitoyl-2-acetyl-sn-glycero-3-phosphocholine The 1-O-triphenylmethyl group was eliminated from 1-O-triphenylmethyl-2-acetyl-sn-glycero-3-phosphocholine by the method stated in Example 5, stage B, and the resulting 2-acetyl-sn-glycero-3-phosphocholine was reacted with palmitic anhydride by the method stated in Example 5, stage C, to give 1-palmitoyl-2-acetyl-sn-glycero-3-phosphocholine.

EXAMPLE 9

(A) 1-O-Triphenylmethyl-2-methoxyacetyl-sn-glycero-3-phosphocholine 316 mg of 1-O-triphenylmethyl-sn-glycero-3-phosphocholine according to Example 1 is reacted by the method stated in Example 5, stage A, with methoxyacetylimidazolide, which was prepared from 90 mg of methoxyacetic acid and 178 mg of carbonyldiimidazole, and the mixture was worked up. 250 mg (69% yield) of pure 1-O-triphenylmethyl-2-methoxyacetyl-sn-glycero-3-phosphocholine is obtained, which gives a single spot in the thin-layer chromatogram (mobile phase: 65:35:5 (v/v/v) chloroform/methanol/25% strength aqueous NH$_3$ solution); $R_f$ value 0.25.

(B) 2-Methoxyacetyl-sn-glycero-3-phosphocholine (C) 1-Stearoyl-2-methoxyacetyl-sn-glycero-3-phosphocholine The 1-O-triphenylmethyl group was eliminated by the method stated in Example 5, stage B, from 1-O-triphenylmethyl-2-methoxyacetyl-sn-glycero-3-phosphocholine, and the resulting 2-methoxyacetyl-sn-glycero-3-phosphocholine is reacted with stearic anhydride as in Example 6 to give 1-stearoyl-2-methoxyacetyl-sn-glycero-3-phosphocholine, and the product is purified by chromatography.

EXAMPLE 10

(A) 1-O-Triphenylmethyl-2-(2'-ethylhexanoyl)-sn-glycero-3-phosphocholine

A solution of 250 mg of 1-O-triphenylmethyl-sn-glycero-3-phosphocholine (according to Example 1) is reacted by the method stated in Example 5, stage A, with 2-ethylhexanoylimidazolide, which was prepared from 144 mg of 2-ethylhexanoic acid and 178 mg of carbonyldiimidazole, and the mixture was worked up. 200 mg (69% yield) of pure 1-O-triphenylmethyl-2-(2'-ethylhexanoyl)-sn-glycero-3-phosphocholine are obtained, the product giving a single spot in the thin-layer chromatogram (mobile phase: 65:35:5 (v/v/v) chloroform/methanol/35% strength $NH_3$); $R_f$ value 0.24.

(B) 2-(2'-Ethylhexanoyl)-sn-glycero-3-phosphocholine (C) 1-Oleoyl-2-(2'-ethylhexanoyl)-sn-glycero-3-phosphocholine The 1-O-triphenylmethyl group was eliminated by the method stated in Example 5, stage B, from 1-O-triphenylmethyl-2-(2'-ethylhexanoyl)-sn-glycero-3-phosphocholine, and the resulting 2-(2'-ethylhexanoyl)-sn-glycero-3-phosphocholine was reacted with oleic anhydride by the method stated in Example 5, stage C, to give 1-oleoyl-2-(2'-ethylhexanoyl)-sn-glycero-3-phosphocholine, and the product was purified by chromatography.

EXAMPLE 11

(A) 1-O-Triphenylmethyl-2-(1'-$^{4}$C)-dodecanoyl-sn-glycero-3-phosphocholine 100 mg of (1'-$^{14}$C)-dodecanoic acid (1 uci/mmol) and 90 mg of carbonyldiimidazole in 3 ml of anhydrous tetrahydrofuran are reacted for 45 minutes at 20° C. The solution of the resulting acylimidazolide is added to 127 mg of 1-O-triphenylmethyl-sn-glycero-3-phosphocholine. After the solvent has been stripped off in vacuo, the residue is dissolved in 1 ml of dimethyl sulfoxide, and the reaction is initiated by adding the catalytic acid acceptor, which has been obtained by dissolving 23 mg of metallic sodium in 18 ml of dimethyl sulfoxide. The reaction mixture is kept at 20° C. for 10 minutes, with occasional shaking, after which it is neutralized by adding 10 ml of aqueous acetic acid all at once. Thereafter, the mixture is extracted with twice 15 ml of chloroform/methanol (2:1, v/v). The combined organic phases are washed successively with 6 ml of chloroform/methanol/aqueous $NH_3$ solution (3:48:47, v/v/v) and 6 ml of chloroform/methanol/water (3:48:47, v/v/v). Stripping off the solvent in vacuo and evaporation in the presence of benzene gives the crude product, which is purified by medium pressure chromatography over silica gel using a chloroform/methanol gradient, 110 mg of pure substance (82% yield) being eluted at a chloroform/methanol ratio of 6:4 (v/v).

The pure substance gives a single spot in the thin-layer chromatogram over silica gel (mobile phase: 65:35:5 (v/v/v) chloroform/methanol/25% strength aqueous $NH_3$ solution); $R_f$ 0.25. The radioactivity is 1 uci/mmol).

$^1$H-NMR spectrum δ in ppm (CDCl$_3$/CD$_3$OD, 2:1, v/v) 0.90 (acyl—Ch$_3$, 3H); 1.26 (($CH_2)_n$, s)16H); 1.66 (H$_2$C—C—CO, m, 2H); 3.16 (H$_3$C—N$^+$, s, 9H); 3.3–4.4 (glycerol and choline—CH$_2$, 8H); 5.23 (glycerol—CH, m, 1H); 7.33 (aromatic, 15H).

(B) 2-(1'-$^{14}$C)-Dodecanoyl-sn-glycero-3-phosphocholine (C) 1-Oleoyl-2-(1'-$^{14}$C)-dodecanoyl-sn-glycero-3-phosphocholine The 1-O-triphenylmethyl group was eliminated by the method stated in Example 5, stage B, from 1-O-triphenylmethyl-2-(2'-$^{14}$C)-dodecanoyl-sn-glycero-3-phosphocholine, and the resulting 2-(1'-$^{14}$C)-dodecanoyl-sn-glycero-3-phosphocholine was reacted with oleic anhydride as in Example 5, stage C, to give 1-oleoyl-2-(2'-$^{14}$C)-dodecanoyl-sn-glycero-3-phosphocholine, and the product was purified by chromatography.

EXAMPLE 12

(A) 1-O-Triphenylmethyl-2-(9',10'-dibromostearoyl)-sn-glycero-3-phosphocholine 300 mg of 1-O-triphenylmethyl-sn-glycero-3-phosphocholine (according to Example 1) is reacted with 1.3 g of 9,10-dibromostearic anhydride in the presence of 300 mg of 4-N,N-dimethylaminopyridine in 20 ml of chloroform for 5 hours at 20° C. by the method stated in Example 8, stage A, and the mixture is worked up. 460 mg (82% yield) of pure 1-O-triphenylmethyl-2-(9',10'-dibromostearoyl)-sn-glycero-3-phosphocholine are obtained, which gives a single spot in the thin-layer chromatogram (mobile phase: 65:35:5 (v/v/v) chloroform/methanol/25% strength aqueous $NH_3$ solution); $R_f$ value 0.3.

(B) 2-(9',10'-Dibromostearoyl)-sn-glycero-3-phosphocholine (C) 1-Stearoyl-2-(9',10'-dibromostearoyl)-sn-glycero-3-phosphocholine The 1-O-triphenylmethyl group was eliminated from 1-O-triphenylmethyl-2-(9',10'-dibromostearoyl)-sn-glycero-3-phosphocholine by the method stated in Example 5, stage B, and the resulting 2-(9',10'-dibromostearoyl)-sn-glycero-3-phosphocholine was reacted with stearic anhydride as in Example 6 to give 1-stearoyl-2-(9',10'-dibromostearoyl)-sn-glycero-3-phosphocholine, and the product was purified by chromatography.

EXAMPLE 13

(A) 1-O-Triphenylmethyl-2-arachidonoyl-sn-glycero-3-phosphocholine 550 mg of 1-O-triphenylmethyl-sn-glycero-3-phosphocholine (according to Example 1) is reacted with 1.50 g of arachidonic anhydride under an argon atmosphere by the method stated in Example 12. After the addition of 15 ml of methanol, the mixture is washed with 9 ml of chloroform/methanol/water (3:48:47, v/v/v), after which the lower phase is brought to dryness in vacuo, and the product is purified by medium pressure chromatography.

750 mg (80% yield) of pure 1-O-triphenylmethyl-2-arachidonoyl-sn-glycero-3-phosphocholine are obtained, which gives a single spot in the thin-layer chromatogram (mobile phase: 65:35:5 (v/v/v) chloroform/methanol/25% strength aqueous $NH_3$ solution); $R_f$ value 0.3.

(B) 2-Arachidonoyl-sn-glycero-3-phosphocholine (C) 1-Stearoyl-2-arachidonoyl-sn-glycero-3-phosphocholine The 1-O-triphenylmethyl group was eliminated from 1-O-triphenylmethyl-2-arachidonoyl-sn-glycero-3-phosphocholine by the method stated in Example 5, stage B, and the resulting 2-arachidonoyl-sn-glycero-3-phosphocholine was reacted with stearic anhydride as in Example 6 to give 1-stearoyl-2-arachidonoyl-sn-glycero-3-phosphocholine, and the product was purified by chromatography.

EXAMPLE 14

(A) 1-O-Triphenylmethyl-2-tetracosanoyl-sn-glycero-3-phosphocholine 316 mg of 1-O-triphenylmethyl-sn-glycero-3-phosphocholine (according to Example 1) is reacted by the method stated in Example 5, stage A, with tetracosanoylimidazolide, which has been prepared from 1.7 g of tetracosanoic acid and 356 mg of carbonyldiimidazole, and the mixture is worked up. 850 mg (62% yield) of pure 1-O-triphenylmethyl-2-tetracosanoyl-sn-glycero-3-phosphocholine are obtained, which gives a single spot in the thin-layer chromatogram (mobile phase: 65:35:5 (v/v/v) chloroform/methanol/25% strength aqueous $NH_3$ solution); $R_f$ value 0.3.

(B) 2-Tetracosanoyl-sn-glycero-3-phosphocholine (C) 1-Oleoyl-2-tetracosanoyl-sn-glycero-3-phosphocholine The 1-O-triphenylmethyl group was eliminated from 1-O-triphenylmethyl-2-tetracosanoyl-sn-glycero-3-phosphocholine by the method stated in Example 5, stage B, and the resulting 2-tetracosanoyl-sn-glycero-3-phosphocholine was reacted with oleic anhydride to give 1-oleoyl-2-tetracosanoyl-sn-glycero-3-phosphocholine, and the product was purified by chromatography, these steps being carried out as in Example 5, stage C.

EXAMPLE 15

(A) 1-O-Triphenylmethyl-2-oleoyl-sn-glycero-3-phospho-(N-triphenylmethyl)-ethanolamine 386 mg of oleic acid and 255 mg of carbonyldiimidazole in 10 ml of tetrahydrofuran are stirred for 45 minutes at room temperature in the absence of moisture. 480 mg of 1-O-triphenylmethyl-sn-glycero-3-phospho-(N-triphenylmethyl)-ethanolamine (according to Example 2) are taken up in the solution of the oleoylimidazolide, after which 3.1 ml of a solution of 41 mg of sodium metal in dimethyl sulfoxide are added. The mixture is allowed to react for 20 minutes at room temperature and is then neutralized with 17.8 ml of 0.1N aqueous acetic acid. It is then taken up in ice water and extracted three times with diethyl ether, the combined organic phases are washed twice with water and dried over $Na_2SO_4$, and the solvent is then stripped off in vacuo. After purification of the crude product by chromatography over silica gel using a petroleum ether/chloroform gradient, 633 mg of the pure target compound are obtained. Thin-layer chromatography of the product over silica gel (mobile phase: 9:1 (v/v) chloroform/methanol) gives a single spot ($R_f$ 0.6).

$^1$H-NMR spectrum: δ ppm ($CDCl_3$) 0.88 (—$CH_3$); 1.26 (—$CH_2$—); 1.8–2.3 (—$CH_2$—$CH_2$—C≡C, —$CH_2$—$CH_2$—C=O); 3.1–4.3 (glycerol and ethanolamine C—H); 5.1 (glycerol $C_2$—C—H, oleoyl HC=CH); 7.25 (triphenylmethyl C—H).

(B) 2-Oleoyl-sn-glycero-3-phospho-(N-triphenylmethyl)-ethanolamine

A solution of 406 mg of 1-O-triphenylmethyl-2-oleoyl-sn-glycero-3-phospho-(N-triphenylmethyl)-ethanolamine in a mixture of 30 ml of methylene chloride and 1 ml of a 20% strength solution of boron trifluoride in methanol is stirred for 30 minutes at 0° C. 30 ml of methylene chloride are then added, the mixture is washed three times with water, and the organic phase is dried over $Na_2SO_4$.

(C) 1-Palmitoyl-2-oleoyl-sn-glycero-3-phospho-(N-triphenylmethyl)-ethanolamine 1.3 g of palmitic anhydride and 230 mg of dimethylaminopyridine are added to the solution of the resulting 2-oleoyl-sn-glycero-3-phospho-(N-triphenylmethyl)-ethanolamine. The reaction mixture is stirred for 6 hours at 20° C. The solvent is then stripped off in vacuo. After the residue has been chromatographed over silica gel using a petroleum ether/chloroform gradient, 361 mg of the pure acylation product are obtained. When subjected to thin-layer chromatography over silica gel (mobile phase: 9:1 (v/v) chloroform/methanol), the compound gives a single spot ($R_f$ 0.6).

$^1$H-NMR spectrum: δ ppm ($CDCl_3$) 0.88 (—$CH_3$); 1.22 (—$CH_2$—); 1.55 (—$CH_2$—C—CO); 1.8–2.3 (—$CH_2$—$CH_2$—C≡, —$CH_2$—C=O); 3.1–4.3 (glycerol and ethanolamine C—H); 5.1 (glycerol=C—H, oleoyl CH=CH); 7.25 (triphenylmethyl C—H).

(D) 1-Palmitolyl-2-oleoyl-sn-glycero-3-phosphoethanolamine

A solution of 190 mg of 1-palmitoyl-2-oleoyl-sn-3-glycero-(N-triphenylmethyl)-ethanolamine in 12 ml of a mixture of 6 ml of methylene chloride and 6 ml of trifluoroacetic acid is left to stand in the absence of moisture for 5 minutes at 0° C. It is then neutralized by adding 23 ml of a six percent strength aqueous ammonia solution all at once. The aqueous phase is separated off and extracted with 2:1 (v/v) chloroform/methanol. The combined organic phases are washed with water. After the solvent has been stripped off in vacuo, the crude product is purified by chromatography over silica gel using a chloroform/methanol gradient. When subjected to thin-layer chromatography over silica gel (mobile phase: 50:25:6 (v/v/v) chloroform/methanol/25% strength aqueous $NH_3$ solution), the compound gives a single spot ($R_f$ 0.5).

EXAMPLE 16

(A) 1-O-Triphenylmethyl-2-linoleoyl-sn-glycero-3-phospho-(N-triphenylmethyl)-ethanolamine 464 mg of linoleic acid and 365 mg of carbonyldiimidazole in 15 ml of tetrahydrofuran are reacted for 45 minutes at 20° C. The solution of the resulting acylimidazolide is added to 530 mg of 1-O-triphenylmethyl-sn-glycero-3-phospho-(N-triphenylmethyl)-ethanolamine (according to Example 2). After the solvent has been stripped off in vacuo, the residue is dissolved in 15 ml of dimethyl sulfoxide, and the reaction is initiated by adding the catalytic acid acceptor, which has been obtained by dissolving 49 mg of metallic sodium in 3.7 ml of dimethyl sulfoxide. The reaction mixture is kept at 20° C. for 20 minutes with occasional shaking, after which it is neutralized with 10.4 ml of aqueous 0.1N acetic acid, added all at once. The mixture is then extracted with twice 20 ml of 2:1 (v/v) chloroform/methanol. The combined organic phases are washed successively with 8 ml of chloroform/methanol/aqueous $NH_3$ solution (3:48:47, v/v/v) and 8 ml of chloroform/methanol/water (3:48:47, v/v/v). Stripping off the solvent in vacuo and evaporating the residue in the presence of benzene gave a crude product which, when purified by medium pressure chromatography over silica gel using a chloroform/methanol gradient, gives 670 mg (92% yield) of the pure compound. In the thin-layer chromatogram over silica gel (mobile phase: 8:3 (v/v) methanol/chloroform), the pure compound gives a single spot; $R_f$ 0.61.

(B) 2-Linoleoyl-sn-glycero-3-phospho-(N-triphenylmethyl)-ethanolamine

The 1-O-triphenylmethyl group is eliminated from 435 g of 1-O-triphenylmethyl-2-linoleoyl-sn-glycero-3-phospho-(N-triphenylmethyl)-ethanolamine by the method stated in Example 15, stage B, using 0.5 ml of a 20% strength solution of boron trifluoride in methanol.

(C) 1-Oleoyl-2-linoleoyl-sn-glycero-3-phospho-(N-triphenylmethyl)-ethanolamine (D) 1-Oleoyl-2-linoleoyl-sn-glycero-3-phosphoethanolamine 2-Linoleoyl-sn-glycero-3-phospho-(N-triphenylmethyl)-ethanolamine is further acylated analogously to the method in Example 15, stage C, by reaction with oleic anhydride, to give 1-oleoyl-2-linoleoyl-sn-glycero-3-phospho-(N-triphenylmethyl)-ethanolamine, and the N-triphenylmethyl radical is eliminated from this analogously to the method stated in Example 15, stage D.

EXAMPLE 17

(A) 1-O-Triphenylmethyl-2-stearoyl-sn-glycero-3-phospho-(N-triphenylmethyl)-ethanolamine was prepared analogously to the method in Example 16, stage A, by reaction of 380 mg of 1-O-triphenylmethyl-sn-glycero-3-phospho-(N-triphenylmethyl)-ethanolamine with 350 mg of stearoylimidazolide.

(B) 2-Stearoyl-sn-glycero-3-phospho-(N-triphenylmethyl)ethanolamine was obtained from the product obtained in stage A by eliminating the 1-O-triphenylmethyl group by the method stated in Example 15, stage B.

(C) 1-Oleoyl-2-stearoyl-sn-glycero-3-phospho-(N-triphenylmethyl)-ethanolamine (D) 1-Oleoyl-2-stearoyl-sn-glycero-3-phosphoethanolamine The 2-stearoyl-sn-glycero-3-phospho-(N-triphenylmethyl)-ethanolamine obtained in stage B is reacted with 1.5 g of oleic anhydride to give 340 mg of 1-oleoyl-2-stearoyl-sn-glycero-3-phospho-(N-triphenyl-methyl)ethanolamine analogously to the method in Example 15, stage C. Detritylation analogous to the method in Example 15, stage D, gives 250 mg of 1-oleoyl-2-stearoyl-sn-glycero-3-phosphoethanolamine; chromatographing this over silica gel using a chloroform/methanol gradient gives 140 mg of pure product, which shows a single spot in the thin-layer chromatogram (mobile phase: 50:25:6 (v/v/v) chloroform/methanol/25% strength aqueous NH$_3$ solution); $R_f$ value 0.5.

EXAMPLE 18

(A) 1-O-Triphenylmethyl-2-acetyl-sn-glycero-3-phospho-(N-triphenylmethyl)-ethanolamine 300 mg of 1-O-triphenylmethyl-sn-glycero-3-phospho-(N-triphenylmethyl)-ethanolamine (according to Example 2) are reacted with 500 ml of acetic anhydride in 5 ml of anhydrous pyridine for 20 hours at 20° C. The mixture is then poured onto 50 ml of ice water and extracted twice with 2:1 (v/v) chloroform/methanol. The combined organic phases are washed twice with 3:48:47 (v/v/v) chloroform/methanol/water, dried over sodium bicarbonate and brought to dryness in vacuo, Residual pyridine is removed by evaporation in the presence of toluene. The crude product is purified by medium pressure chromatography over silica gel using a chloroform/methanol gradient. The pure substance obtained (128 mg, 40% yield) gives a single spot in the thin-layer chromatogram over silica gel (mobile phase: 8:2 (v/v) chloroform/methanol); $R_f$ value 0.50.

$^1$H-NMR spectrum δ ppm (CDCl$_3$/CD$_3$OD 2:1 v/v); 2.0 (H$_3$C—CO, s, 3H); 2.8–4.2 (glycerol and choline—CH$_2$); 5.16 (glycerol—CH, m, 1H); 7.23 (aromatic, 3OH)

1-O-Triphenylmethyl-2-acetyl-sn-glycero-3-phospho-(N-triphenylmethylamine)-ethanolamine was converted analogously to the methods in stages B, C and D of Example 15 to give the following further products:

(B) 2-Acetyl-sn-glycero-3-phospho-(N-triphenylmethyl)ethanolamine (C) 1-Palmitoyl-2-acetyl-sn-glycero-3-phospho-(N-triphenylmethyl)-ethanolamine (D) 1-Palmitoyl-2-acetyl-sn-glycero-3-phosphoethanolamine

EXAMPLE 19

(A) 1-O-Triphenylmethyl-2-propionyl-sn-glycero-3-phospho-(N-triphenylmethyl)-ethanolamine 450 mg of 1-O-triphenylmethyl-sn-glycero-3-phospho-(N-triphenylmethyl)-ethanolamine (according to Example 2) were reacted with 900 mg of propionic anhydride in 10 ml of pyridine at 30° C. to give 1-O-triphenylmethyl-2-propionyl-sn-glycero-3-phospho-(N-triphenylmethyl)-ethanolamine, the mixture was worked up and the product was purified, these steps being carried out analogously to the method in Example 18, stage A.

Yield: 220 mg (45% of theory); $R_f$ value 0.5. The product obtained was converted analogously to the methods in Example 15, stages B, C and D, to give the following compounds:

(B) 2-Propionyl-sn-glycero-3-phospho-(N-triphenylmethyl)ethanolamine (C) 1-Palmitoyl-2-propionyl-sn-glycero-3-phospho-(N-triphenylmethyl)-ethanolamine (D) 1-Palmitoyl-2-propionyl-sn-glycero-3-phosphoethanolamine

EXAMPLE 20

(A) 1-O-Triphenylmethyl-2-butyryl-sn-glycero-3-phospho-(N-triphenylmethyl)-ethanolamine 500 mg of 1-O-triphenylmethyl-sn-glycero-3-phospho-(N-triphenylmethyl)-ethanolamine (according to Example 2) was acylated with butyrylimidazolide, which was obtained from 132 mg of butyric acid and 267 mg of carbonyldiimidazole, the mixture was worked up and the product was purified, these steps being carried out as in Example 16, stage A. The product obtained (300 mg, 56% yield; $R_f$ value 0.52, over silica gel, mobile phase: 8:2 (v/v) chloroform/methanol) was reacted further analogously to the methods in Example 15, stages B, C and D, to give the following compounds:

(B) 2-Butyryl-sn-glycero-3-phospho-(N-triphenylmethyl)ethanolamine (C) 1-Palmitoyl-2-butyryl-sn-glycero-3-phospho-(N-triphenylmethyl)-ethanolamine (D) 1-Palmitoyl-2-butyryl-sn-glycero-3-phosphoethanolamine

EXAMPLE 21

(A) 1-O-Triphenylmethyl-2-isobutyryl-sn-glycero-3-phospho-(N-triphenylmethyl)-ethanolamine 500 mg of 1-O-triphenylmethyl-sn-glycero-3-phospho-(N-triphenylmethyl)-ethanolamine (according to Example 2) was acylated with isobutyrylimidazolide, which was obtained from 132 mg of isobutyric acid and 267 mg of carbonyldiimidazole, the mixture was worked up and the product was purified, these steps being carried out as in Example 16, stage A. The product obtained (272 mg, 50% yield; $R_f$ value 0.53, over silica gel, mobile phase: 8:2 (v/v) chloroform/methanol) gives the following spectroscopic data:

$^1$H-NMR spectrum: δ ppm (CDCl$_3$/CD$_3$OD, 2:1, v/v) 1.2 (CH$_3$, 6H); 2.5–3.9 (glycerol and choline CH$_2$, 8H); 5.26 (glycerol—CH, m, 1H); 7.23 (aromatic, 30H).

1-O-Triphenylmethyl-2-isobutyryl-sn-glycero-3-phospho-(N-triphenylmethyl)-ethanolamine was converted analogously to Example 16, stages B, C and D, to give the following compounds:

(B) 2-Isobutyryl-sn-glycero-3-phospho-(N-triphenylmethyl)ethanolamine (C) 1-Oleoyl-2-isobutyryl-sn-glycero-3-phospho-(N-triphenylmethyl)-ethanolamine (D) 1-Oleoyl-2-isobutyryl-sn-glycero-3-phosphoethanolamine

EXAMPLE 22

(A) 1-O-Triphenylmethyl-2-(3'-trifluoromethylbutyryl)-sn-glycero-3-phospho-(N-triphenylmethyl)-ethanolamine 900 mg of 1-O-triphenylmethyl-sn-glycero-3-phospho-(N-triphenylmethyl)-ethanolamine (according to Example 2) and 500 mg of 3-trifluoromethylbutyryl anhydride in 50 ml of methylene chloride were stirred for 4 hours at 20° C. after 300 mg of 4-N,N-dimethylaminopyridine had been added. After the addition of water, the mixture is extracted by shaking, and the organic phase is dried over Na$_2$SO$_4$ and evaporated down in vacuo. After the crude product has been purified by medium pressure chromatography over silica gel using a chloroform/methanol gradient in the presence of 0.5% by volume of aqueous NH$_3$ solution, 820 mg (76% yield; $R_f$ value 0.50, over silica gel, mobile phase: 8:2 (v/v) chloroform/methanol) of 1-O-triphenylmethyl-2-(3'-trifluoromethylbutyryl)-sn-glycero-3-phospho-(N-triphenylmethyl)-ethanolamine are obtained. This product was converted analogously to Example 15, stages B, C and D, to give the following compounds:

(B) 2-(3'-Trifluoromethylbutyryl)-sn-glycero-3-phospho-(N-triphenylmethyl)-ethanolamine (C) 1-Palmitoyl-2-(3'-trifluoromethylbutyryl)-sn-glycero-3-phospho-(N-triphenylmethyl)-ethanolamine (D) 1-Palmitoyl-2-(3'-trifluoromethylbutyryl)-sn-glycero-3-phosphoethanolamine

EXAMPLE 23

(A) 1-O-Triphenylmethyl-2-(2'-butylhexanoyl)-sn-glycero-3-phospho-(N-triphenylmethyl)-ethanolamine 430 mg of 1-O-triphenylmethyl-sn-glycero-3-phospho-(N-triphenylmethyl)-ethanolamine (according to Example 2) was acylated with 2-butylhexanoylimidazolide, which was obtained from 200 mg of 2-butylhexanoic acid and 210 mg of carbonyldiimidazole, the mixture was worked up and the product was purified, these steps being carried out as in Example 16, stage A. The product obtained (370 mg, 70% yield; $R_f$ value 0.55, over silica gel, mobile phase: 8:2 (v/v) chloroform/methanol) was reacted further analogously to the methods in Example 15, stages B, C and D, to give the following compounds:

(B) 2-(2'-Butylhexanoyl)-sn-glycero-3-phospho-(N-triphenylmethyl)-ethanolamine (C) 1-Palmitoyl-2-(2'-butylhexanoyl)-sn-glycero-3-phospho-(N-triphenylmethyl)-ethanolamine (D) 1-Palmitoyl-2-(2'-butylhexanoyl)-sn-glycero-3-phosphoethanolamine

EXAMPLE 24

(A) 1-O-Triphenylmethyl-2-arachidonoyl-sn-glycero-3-phospho-(N-triphenylmethyl)-ethanolamine 500 mg of 1-O-triphenylmethyl-sn-glycero-3-phospho-(N-triphenylmethyl)-ethanolamine (according to Example 2) and 890 mg of arachidonic anhydride in 50 ml of methylene chloride were stirred for 4 hours at 20° C. after 300 mg of 4-N,N-dimethylaminopyridine had been added. After the addition of water, the mixture is extracted by shaking, and the organic phase is dried over Na$_2$SO$_4$ and evaporated down in vacuo. After purification of the crude product by medium pressure chromatography over silica gel using a chloroform/methanol gradient in the presence of 0.5% by volume of aqueous NH$_3$, 520 mg (82% yield; $R_f$ value 0.61, over silica gel, mobile phase: 8:2 (v/v) chloroform/methanol) of 1-O-triphenylmethyl-2-arachidonyl-sn-glycero-3-phospho-(N-triphenylmethyl)-ethanolamine are obtained. This product was converted analogously to Example 15, stages B, C and D, to give the following compounds:

(B) 2-Arachidonoyl-sn-glycero-3-phospho-(N-triphenylmethyl)-ethanolamine (C) 1-Palmitoyl-2-arachidonoyl-sn-glycero-3-phospho-(N-triphenylmethyl)-ethanolamine (D) 1-Palmitoyl-2-arachidonoyl-sn-glycero-3-phosphoethanolamine

EXAMPLE 25

(A) 1-O-Triphenylmethyl-2-tetracosanoyl-sn-glycero-3-phospho-(N-triphenylmethyl)-ethanolamine 500 mg of 1-O-triphenylmethyl-sn-glycero-3-phospho-(N-triphenylmethyl)-ethanolamine (according to Example 2) was acylated with tetracosanoylimidazolide, which was obtained from 1.57 g of tetracosanoic acid and 267 mg of carbonyldiimidazole, the mixture was worked up and the product was purified, these steps being carried out as in Example 16, stage A. The product obtained (640 mg, 90% yield; $R_f$ value 0.6, over silica gel, mobile phase: 8:2 (v/v) chloroform/methanol) was reacted further analogously to the methods in Example 15, stages B, C and D, to give the following compounds:

(B) 2-Tetracosanoyl-sn-glycero-3-phospho-(N-triphenylmethyl)-ethanolamine (C) 1-Palmitoyl-2-tetracosanoyl-sn-glycero-3-phospho-(N-triphenylmethyl)-ethanolamine (D) 1-Palmitoyl-2-tetracosanoyl-sn-glycero-3-phosphoethanolamine

EXAMPLE 26

(C) 1-Stearoyl-2-oleoyl-sn-glycero-3-phospho-(N-triphenylmethyl)-ethanolamine 3.5 g of stearic anhydride and 625 mg of 4-N,N-dimethylaminopyridine are added to a solution, in 150 ml of methylene chloride, of 2-oleoyl-sn-glycero-3-phospho- (N-triphenylmethyl)-ethanolamine, which was obtained from 1.1 g of 1-O-triphenylmethyl-2-oleoyl-sn-glycero-3-phospho-(N-triphenylmethyl)-ethanolamine (see Example 15, stages A and B). The reaction mixture was stirred for 3 hours at 20° C., after which 45 ml of chloroform/methanol/water (3:48:47, v/v/v) and 75 ml of methanol were added. After extraction by shaking, the lower phase is separated off, and washed with twice 45 ml of chloroform/methanol/aqueous ammonia (3:48:47, v/v/v) and once with chloroform/methanol/water (3:48:47, v/v/v). After the solvent has been stripped off in vacuo, the crude product is purified by medium pressure chromatography over silica gel using a chloroform/methanol gradient, 990 mg (89% yield, $R_f$ value 0.6, over silica gel, mobile phase: 9:1 (v/v) chloroform/methanol) of pure substance being obtained.

(D) 1-Stearoyl-2-oleoyl-sn-glycero-3-phosphoethanolamine 1 g of 1-stearoyl-2-oleoyl-sn-glycero-3-phospho-(N-triphenylmethyl)-ethanolamine in 30 ml of trifluoroacetic acid is left to stand for 5 minutes at 0° C. Working up is carried out as in Example 15, stage D. 550 mg of pure substance (72% yield) are obtained, which gives a single spot in the thin-layer chromatogram over silica gel (mobile phase: 50:25:6 (v/v/v) chloroform/methanol/25% strength $NH_3$); $R_f$ value 0.5.

EXAMPLE 27

(C) 1-Stearoyl-2-linoleoyl-sn-glycero-3-phospho-(N-triphenylmethyl)-ethanolamine
(D) 1-Stearoyl-2-linoleoyl-sn-glycero-3-phosphoethanolamine 2.2 g of stearic anhydride and 390 mg of 4-N,N-dimethylaminopyridine are added to 2-linoleoyl-sn-glycero-3-phospho-(N-triphenylmethyl)-ethanolamine, obtained from 700 mg of 1-O-triphenylmethyl-2-linoleoyl-sn-glycero-3-phospho-(N-triphenylmethyl)-ethanolamine (see Example 16, stages A and B), in methylene chloride, and the mixture is stirred for 3 hours at room temperature. The product obtained is reacted with trifluoroacetic acid, and the product is purified, these steps being carried out as described in Example 15, stage D.

This procedure gives 250 mg of pure 1-stearoyl-2-linoleoyl-sn-glycero-3-phosphoethanolamine, which shows a single spot in the thin-layer chromatogram over silica gel (mobile phase: chloroform/methanol as in Example 26); $R_f$ value 0.5.

What we claim is:

1. Method for preparing 1,2-diacyl-sn-glycero-3-phosphocholines and 1,2-diacyl-sn-glycero-3-phosphoethanolamines of the formula

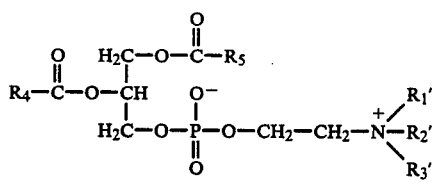

in which $R_1'$, $R_2'$ and $R_3'$ are identical and in each case denote either 3 hydrogen atoms or 3 methyl groups, and
$R_4$ and $R_5$ are different and independently of one another denote a straight chain or branched $C_1$ to $C_{24}$-alkyl radical, a straight chain or branched $C_1$ to $C_{24}$-alkyl radical substituted by one or more halogen atoms or alkoxy groups, a straight chain or branched monounsaturated or polyunsaturated $C_3$ to $C_{24}$-alkenyl radical or a straight chain or branched monounsaturated or polyunsaturated $C_3$ to $C_{24}$-alkenyl radical substituted by one or more halogen atoms or alkoxy groups, which method comprises (a) acylating a compound of the formula:

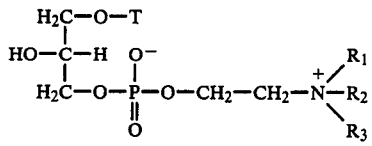

in which

T denotes an unsubstituted or substituted triphenylmethyl group wherein the substituent is $C_{1-6}$ alkyl, $C_{1-6}$ alkoxy or halogen and the radicals $R_1$, $R_2$ and $R_3$ either are identical and each represent a methyl group or are different, in which case two of the radicals $R_1$, $R_2$ and $R_3$ always denote hydrogen and the third radical represents an unsubstituted or substituted triphenylmethyl group wherein the substituent is $C_{1-6}$ alkyl, $C_{1-6}$ alkoxy or halogen, by reaction with an acylating derivative of a carboxylic acid of the formula $R_4COOH$ to give a compound of the formula:

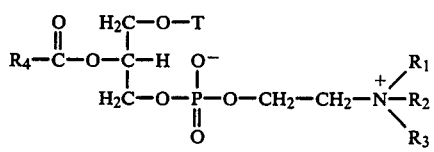

wherein $R_4$ and T are as defined above and $R_1$, $R_2$ and $R_3$ either are identical and each represent a methyl group or are different, in which case two of the radicals $R_1$, $R_2$ and $R_3$ always denote hydrogen and the third radical represents an unsubstituted or substituted triphenylmethyl group, (b) eliminating the 1-O-triphenylmethyl group from the resulting compound of formula V by the action of an acid, with the proviso that, in the case of compounds of formula V in which one of the radicals $R_1$, $R_2$ and $R_3$ is a triphenylmethyl group, the acid is a Lewis acid, with formulation of a 2-acyl-sn-glycero-3-phosphcholine or a 2-acyl-sn-glycero-3-phospho-N-triphenylmethyl)-ethanolamine of the formula:

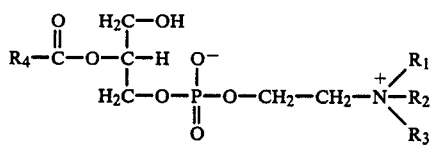

in which $R_1$, $R_2$, $R_3$ and $R_4$ have the meaning given above
(c) acylating the compound of the formula VI by reaction with an acylating derivative of a carboxylic acid of the formula $R_5COOH$ to give a 1,2-diacyl-sn-glycero-3-phosphocholine or 1,2-diacyl-sn-glycero-3-phospho-(N-triphenylmethyl)-ethanolamine of the formula:

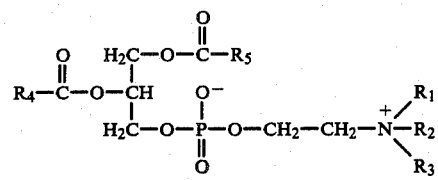
VII
in which
R$_1$, R$_2$ and R$_3$ are as defined in formula V, and
R$_4$ and R$_5$ have the meaning given in formula IV, and
(d) eliminating any N-triphenylmethyl group present in the compound of formula VII by the action of an acid in an aprotic solvent.
* * * * *